US006450974B1

(12) United States Patent
Kim et al.

(10) Patent No.: US 6,450,974 B1
(45) Date of Patent: Sep. 17, 2002

(54) METHOD OF ISOLATING SURFACE TENSION AND YIELD STRESS IN VISCOSITY MEASUREMENTS

(75) Inventors: Sangho Kim, Philadelphia, PA (US); Sehyun Shin, Bryn Mawr, PA (US); Young I. Cho, Cherry Hill, NJ (US)

(73) Assignee: Rheologics, Inc., Exton, PA (US)

( * ) Notice: Subject to any disclaimer, the term of this patent is extended or adjusted under 35 U.S.C. 154(b) by 160 days.

(21) Appl. No.: 09/708,137

(22) Filed: Nov. 8, 2000

Related U.S. Application Data

(63) Continuation-in-part of application No. 09/573,267, filed on May 18, 2000, now Pat. No. 6,402,703, which is a continuation-in-part of application No. 09/439,795, filed on Nov. 12, 1999, now Pat. No. 6,322,524, which is a continuation-in-part of application No. 08/919,906, filed on Aug. 28, 1997, now Pat. No. 6,019,735.

(51) Int. Cl.[7] .................................................. A61B 5/00
(52) U.S. Cl. ........................................ 600/573; 73/64.48
(58) Field of Search ................................ 600/573–574, 600/575, 576, 577, 578, 579, 580; 73/64.48, 64.49, 64.5, 64.51, 64.52

(56) References Cited

U.S. PATENT DOCUMENTS

| | | |
|---|---|---|
| 1,810,992 A | 6/1931 | Dallwitz-Wegner |
| 2,343,061 A | 2/1944 | Irany |
| 2,696,734 A | 12/1954 | Brunstrum et al. |
| 2,700,891 A | 2/1955 | Shafer |
| 2,934,944 A | 5/1960 | Eolkin |
| 3,071,961 A | 1/1963 | Heigl et al. |
| 3,116,630 A | 1/1964 | Piros |
| 3,137,161 A | 6/1964 | Lewis et al. |
| 3,138,950 A | 6/1964 | Welty et al. |
| 3,277,694 A | 10/1966 | Cannon et al. |

(List continued on next page.)

FOREIGN PATENT DOCUMENTS

| | | |
|---|---|---|
| EP | 0 654 286 A1 | 12/1994 |
| WO | WO 92/15878 | 9/1992 |
| WO | WO 94/20832 | 9/1994 |
| WO | WO 99/10724 | 3/1999 |

OTHER PUBLICATIONS

Levenson, et al., Cigarette Smoking & Hypertension, Atherosclerosis V. 7, 572–577, 1987.

Rillaerts, et al., Blood viscosity in Human Obesity; relation to glucose Tolerance and Insulin Status, Internl Jnl. Of Obesity, V. 13, 739–741, 1989.

Rosenson, R., Viscosity & Ischemic Heart Disease, Jnl. Of Vascular Medicine & Biol., V. 4, 206–212, 1993.

(List continued on next page.)

*Primary Examiner*—Kevin Shaver
*Assistant Examiner*—Pamela Wingood
(74) *Attorney, Agent, or Firm*—Caesar, Rivise, Bernstein, Cohen & Pokotilow, Ltd.

(57) ABSTRACT

A method for isolating the effects of surface tension and/or yield stress of a fluid that is flowing in a U-shaped tube wherein one or both legs of the U-shaped tube is monitored over time for the changing height of the respective fluid columns therein. A portion of the U-shaped tube comprises a flow restrictor, e.g., a capillary tube, of known dimensions. Monitoring one or both of the moving fluid columns over time permits the determination of the viscosity of the fluid flowing therein over a range of shear rates from the difference in fluid column heights. However, it is necessary to isolate the effects of surface tension and/or yield stress to obtain an accurate viscosity determination. The method provides one manner in which the surface tension effect can be subtracted from the difference in fluid column heights and then any yield stress effect can then be determined. Alternatively, the method also provides a process by which both the surface tension effect and yield stress effect can be determined simultaneously.

16 Claims, 2 Drawing Sheets

U.S. PATENT DOCUMENTS

| | | |
|---|---|---|
| 3,286,511 A | 11/1966 | Harkness |
| 3,342,063 A | 9/1967 | Smythe et al. |
| 3,435,665 A | 4/1969 | Tzentis |
| 3,520,179 A | 7/1970 | Reed |
| 3,604,247 A | 9/1971 | Gramain et al. |
| 3,666,999 A | 5/1972 | Moreland, Jr. et al. |
| 3,680,362 A | 8/1972 | Geerdes et al. |
| 3,699,804 A | 10/1972 | Gassmann et al. |
| 3,713,328 A | 1/1973 | Aritomi |
| 3,720,097 A | 3/1973 | Kron |
| 3,782,173 A | 1/1974 | Van Vessem et al. |
| 3,839,901 A | 10/1974 | Finkle et al. |
| 3,853,121 A | 12/1974 | Mizrachy et al. |
| 3,864,962 A | 2/1975 | Stark et al. |
| 3,908,441 A | 9/1975 | Virloget |
| 3,911,728 A | 10/1975 | Fixot |
| 3,952,577 A | 4/1976 | Hayes et al. |
| 3,967,934 A | 7/1976 | Seitz et al. |
| 3,990,295 A | 11/1976 | Renovanz et al. |
| 3,999,538 A | 12/1976 | Philpot, Jr. |
| 4,083,363 A | 4/1978 | Philpot, Jr. |
| 4,149,405 A | 4/1979 | Ringrose |
| 4,165,632 A | 8/1979 | Weber et al. |
| 4,193,293 A | 3/1980 | Cavallari |
| 4,207,870 A | 6/1980 | Eldridge |
| 4,302,965 A | 12/1981 | Johnson et al. |
| 4,341,111 A | 7/1982 | Husar |
| 4,417,584 A | 11/1983 | Cathignol et al. |
| 4,426,878 A | 1/1984 | Price et al. |
| 4,432,761 A | 2/1984 | Dawe |
| 4,461,830 A | 7/1984 | Philpot, Jr. |
| B13,999,538 | 7/1984 | Philpot, Jr. |
| 4,517,830 A | 5/1985 | Gunn et al. |
| 4,519,239 A | 5/1985 | Kiesewetter et al. |
| 4,554,821 A | 11/1985 | Kiesewetter et al. |
| 4,616,503 A | 10/1986 | Plungis et al. |
| 4,637,250 A | 1/1987 | Irvine, Jr. et al. |
| 4,643,021 A | 2/1987 | Mattout |
| 4,680,957 A | 7/1987 | Dodd |
| 4,680,958 A | 7/1987 | Ruelle et al. |
| 4,750,351 A | 6/1988 | Ball |
| 4,819,772 A | 4/1989 | Rubel |
| 4,856,322 A | 8/1989 | Langrick et al. |
| 4,858,127 A | 8/1989 | Kron et al. |
| 4,884,577 A | 12/1989 | Merrill |
| 4,899,575 A | 2/1990 | Chu et al. |
| 4,947,678 A | 8/1990 | Hori et al. |
| 5,099,698 A | 3/1992 | Kath et al. |
| 5,142,899 A | 9/1992 | Park et al. |
| 5,181,415 A | 1/1993 | Esvan et al. |
| 5,222,497 A | 6/1993 | Ono |
| 5,224,375 A | 7/1993 | You et al. |
| 5,257,529 A | 11/1993 | Taniguchi et al. |
| 5,271,398 A | 12/1993 | Schlain et al. |
| 5,272,912 A | 12/1993 | Katsuzaki |
| 5,327,778 A | 7/1994 | Park |
| 5,333,497 A | 8/1994 | Br nd Dag A. et al. |
| 5,365,776 A | 11/1994 | Lehmann et al. |
| 5,421,328 A | 6/1995 | Bedingham |
| 5,443,078 A | 8/1995 | Uflacker |
| 5,447,440 A | 9/1995 | Davis et al. |
| 5,491,408 A | 2/1996 | Rousseau |
| 5,494,639 A | 2/1996 | Grzegorzewski |
| 5,549,119 A | 8/1996 | Solar |
| 5,629,209 A | 5/1997 | Braun, Sr. et al. |
| 5,686,659 A | 11/1997 | Neel et al. |
| 5,725,563 A | 3/1998 | Klotz |
| 5,792,660 A | 8/1998 | Spillert et al. |
| 5,837,885 A | 11/1998 | Goodbread et al. |
| 6,039,078 A | 3/2000 | Tamari |
| H93 H | 7/1986 | Matta et al. |

OTHER PUBLICATIONS

Letcher, et al., Direct Relationship Between Blood Pressure & Blood Viscosity in Normal & Hypertensive Subjects, Am. Jnl of Med. V. 70, 1195–1203, Jun. 1981.

Zwick, K.J., The Fluid Mechanics of Bonding with Yield Stress Exposies, Dissortation, Un. Of Penn., PA, USA, 1–142, 1996.

Yarnell, et al., Fibrinogen, viscosity & White Blood Cell Count are Major Risk Factors for Ischemic Heart Disease, Circulation, V. 83, No. 3, Mar. 1991.

Tangney, et al., Postprandial changes in Plasma & Serum Viscosity & Plasma Lipids & Lipoproteins after an acute test meal, Am. Jnl. Of Clin. Nutrition V. 65, 36–40, 1997.

Seplowitz, et al., Effects of Lipoproteins on Plasma Viscosity, Atherosclerosis, V. 38, 89–95, 1981.

Rosenson, et al., Hyperviscosity Syndrome in Hypercholesterolemic Patient with Primary Biliary Cirrhosis, Gastroenterology, V. 98, No. 5, 1990.

Lowe, et al., Blood Viscosity & Risk of Cardiovascular Events: the Edinburgh Artery Study, British Jnl. Of Haematology, V. 96, 168–173, 1997.

Koenig, W., Blood Rheology Assoc. with Cardiovascular Risk Factors & Chronic Cardiovascular Diseases: Results of an Epidemiologic Cross Sectional Study, Am. Coll. Of Angiology, Paradise Is., Bahamas, Oct. 1997.

Hell, K., Importance of Blood Viscoelasticity in Arteriosclerosis, Internl Coll. Of Angiology, Montreux, Switzerland, Jul. 1987.

Delaunois, A., Thermal method for Continuous Blood velocity Measurements in Large Blood Vessels & Cardiac Output Determination, Medical & Biological Engineering, Mar. 1973, V. 11, 201–205.

Nerem, et al., Fluid Mechanics in Atherosclerosis, Handbook of Bioengineering, Chp. 21, 20.24 to 21.22.

Litt, et al., Theory & Design of Disposable Clinical Blood Viscometer, Biorheology, V. 25, 697–712, 1988.

Cooke, et al., Automated Measurement of Plasma Viscosity by Capillary Viscometer, J. Clin. Path., vol. 341, 1213–1216, 1988.

Jiminez, et al., A novel computerized Viscometer/rheometer, Rev. sci. Instrum. V. 65 (1), 229–241, Jan. 1994.

Harkness, A New Instrument for Measurement of Plasma–Viscosity, Med. & Biol. Engineering, Sep. 1976.

Pringle, et al., Blood Viscosity & Raynaud's Disease, The Lancet, May 1965.

Walker, et al., Measurement of Blood Viscosity using a conicylindrical viscometer, Med. & Biol. Engineering, Sep.1976.

Oguraa, et al., Measurement of Human Red Blood Cell Deformability using Single Micropore on a Thin Si3N4 Film, IEEE Transactions on Biomedical Engineering, V. 38, No. 9, Aug. 1991.

Hausler, et al., A Newly Designed Oscillating Viscometer for Blood Viscosity Measurements, 1999, V. 33, No. 4, Biorheology, pp. 397–404.

Martin, et al., Apparent Viscosity of Whole Human Blood at Various Hydrostatic Pressures I. Studies on Anticoagulated Blood Employing new Capillary Viscometer, Biorheology 3–12, V. 11, 1978.

Rheinhardt, et al., Rheologic Measurements on Small Samples with a New Capillary Viscometer, J.Lab.And Clin. Med., 921–931, Dec. 1984.

Chmiel, A New Capillary Viscometer for Clinical use, Biorheology, 301–307, V. 12, 1979.

Pall Corporation, Pall BPF4 High Efficiency Leukocyte Removal Blood Processing Filter System, Pall Biomedical Products Corporation 1993.

Qamar, et al., The Goldman Algorithm Revisited: Prospective E#valuation of Computer Derived Algorithm Vs. Unaided Physician Judgement in Suspected Acute Myocardial Inf., AM. Hrt J. 138, V. 4, 705–709, 1999.

Leonhardt, et al., Studies of Plasma Viscosity in Primary Hyperlipoproteinaemia, Atherosclerosis, V.28, 29–40, 1977.

Kameneva, et al., Red Blood Cell Aging & Risk of Cardiovascular Diseases, Nov. 1977.

METHOD OF ISOLATING SURFACE TENSION AND YIELD STRESS IN VISCOSITY MEASUREMENTS

BACKGROUND OF THE INVENTION

This application is a Continuation-In-Part of application Ser. No. 09/573,267, filed May 18, 2000, now U.S. Pat. No. 6,402,703 which is a Continuation-in-Part of application Ser. No. 09/439,795, filed Nov. 12, 1999, now U.S. Pat. No. 6,322,524 both of which are entitled DUAL RISER/SINGLE CAPILLARY VISCOMETER, which is turn is a Continuation-In-Part of application Ser. No. 08/919,906 filed Aug. 28,1997 entitled VISCOSITY MEASURING APPARATUS AND METHOD OF USE, now U.S. Pat. No. 6,019,735, all of which are assigned to the same Assignee, namely Visco Technologies, Inc. as the present invention and all of whose entire disclosures are incorporated by reference herein.

FIELD OF INVENTION

This invention relates generally to the field of measuring the viscosity of liquids, and more particularly, to a method of isolating the surface tension and yield stress effects when determining the viscosity of a liquid using a U-shaped scanning capillary tube viscometer.

BACKGROUND OF THE INVENTION

In a scanning capillary tube viscometer, a U-shaped tube is used where one portion of the U-shaped tube is formed by a flow restrictor, e.g., capillary tube. One leg of the U-shaped tube supports a falling column of fluid and the other leg supports a rising column of fluid Furthermore, movement of either one or both of these columns is monitored, hence the term "scanning." See FIG. 1. It should be understood that the term "scanning," as used in this Specification, also includes the detection of the change in mass (e.g., weight) in each of the columns. Thus, all manners of detecting the change in the column mass, volume, height, etc. is covered by the term "scanning."

In order to measure liquid viscosity using a U-shaped scanning capillary tube viscometer, the pressure drop across the capillary tube has to be precisely estimated from the height difference between the two fluid columns in the respective legs of the U-shaped tube. However, under normal circumstances, the height difference, $\Delta h(t)$, contains the effects of surface tension and yield stress. Therefore, the contributions of the surface tension ($\Delta h_{st}$) and yield stress ($\tau_y$) to $\Delta h(t)$, have to be taken into account, or isolated. Here, $\Delta h(t)$ is equal to $h_1(t)-h_2(t)$.

The magnitude of the surface tension of a liquid in a tube differs greater depending on the condition of the tube wall. Normally, the surface tension reported in college textbooks are measured from a perfectly wet tube. However, in reality, the falling column has a perfectly wet surface while the rising column has a perfectly dry surface. When the tube is completely dry, the value of the surface tension from the same tube can be substantially different from that measured from a perfectly wet tube. Hence, there is a pronounced effects of the surface tension on the overall height difference between the two columns. The height difference caused by the surface tension can be significantly greater than the experimental resolution required for the accuracy of viscosity measurement. For example, the difference between surface tensions of two columns in the U-shaped tube can produce the height difference, $\Delta h_{st}$, of 3.5 mm where the height difference, $\Delta h$ (t), must be measured as accurately as 0.1 mm. Thus, it is extremely important to isolate the effect of the surface tension from the viscosity measurement.

Similarly, the effect of yield stress, $\tau_y$, must be isolated from the viscosity measurement.

Thus, there remains a need for accounting for, or isolating, the surface tension and yield stress in viscosity measurements when using a scanning capillary tube viscometer.

SUMMARY OF THE INVENTION

A method for isolating the effect of surface tension on a fluid that is flowing in a U-shaped tube having a flow restrictor (e.g., a capillary tube) forming a portion of said U-shaped tube. The fluid forms a falling column of fluid, having a first height that changes with time, in a first leg of the U-shaped tube and a rising column of fluid, having a second height that changes with time, in a second leg of said U-shaped tube. The method comprises the steps of: (a) detecting the difference between the first and second heights over time; and (b) subtracting a term representing surface tension from the difference.

A method of isolating the effect of surface tension on a fluid and the effect of yield stress of a fluid that is flowing in a U-shaped tube having a flow restrictor forming a portion of said U-shaped tube. The fluid forms a falling column of fluid, having a first height that changes with time, in a first leg of said U-shaped tube and a rising column of fluid, having a second height that changes with time, in a second leg of said U-shaped tube. The method comprises the steps of: (a) detecting the difference between the first and second heights over time for generating falling column data and rising column data; (b) curve fitting an equation using the falling column data and the rising column data to determine: (1) a term representing surface tension; and (2) a term representing the yield stress.

DESCRIPTION OF THE DRAWINGS

The invention of this present application will be readily appreciated as the same becomes better understood by reference to the following detailed description when considered in connection with the accompanying drawings wherein.

DESCRIPTION OF THE PREFERRED EMBODIMENT OF THE INVENTION

Figure 1:
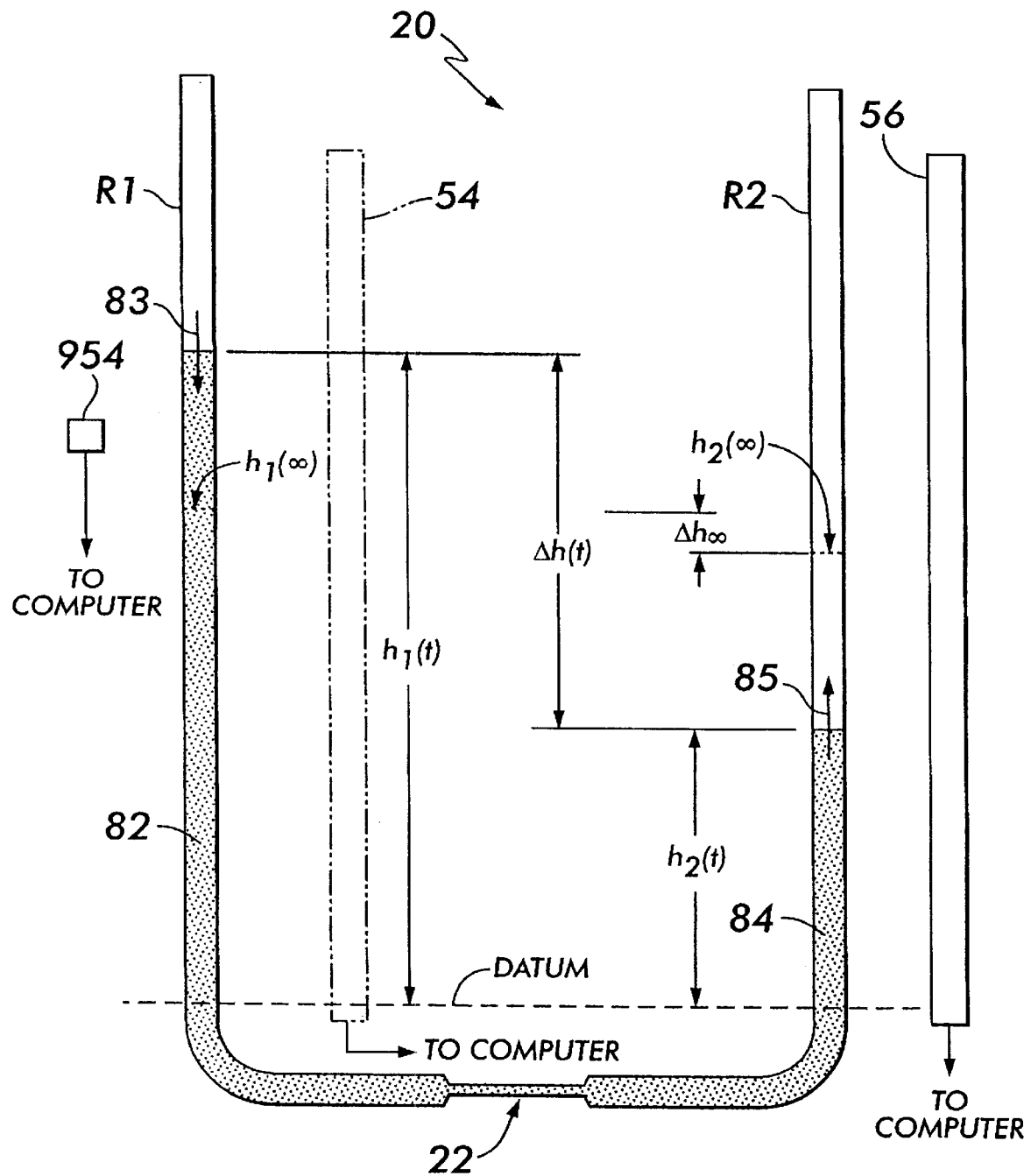
FIG. 1 is a functional diagram of a test fluid flowing in a U-shaped tube having a flow restrictor therein and with column level detectors and a single point detector monitoring the movement of the fluid.

Referring now in detail to the various figures of the drawing wherein like reference characters refer to like parts, there is shown at 20 a U-tube structure comprising a first leg (e.g., a first riser tube) R1, a flow restrictor 22 (e.g., a capillary tube) and a second leg (e.g., second riser tube) R2. It should be understood that the preferred embodiment of the U-tube structure has the flow restrictor forming the horizontal portion at the bottom of the U-tube that connects the two legs together. However, it is within the broadest scope of this invention to include the positioning of the flow restrictor in either one of the legs themselves.

The apparatus 20 uses column level detectors 54/56 for detecting the movement (e.g., the heights, h) of the columns of fluid in the legs of the U-tube: a falling column of fluid 82 and a rising column of fluid 84, as indicated by the respective arrows 83 and 85. The details of such types of detectors are disclosed in application Ser. No. 09/439,795, now U.S. Pat. No. 6,322,524 filed on Nov. 12, 1999 and application Ser. No. 09/573,267, now U.S. Pat. No. 6,403,703 filed on May 18, 2000, now U.S. Pat. No. 6,403,703 both of which are entitled DUAL RISER/SINGLE CAPILLARY VISCOMETER, both of which are assigned to the same Assignee of the present invention, namely Visco Technologies, Inc. and both of whose entire disclosures are incorporated by reference herein Thus, the details of these detectors are not repeated here. Furthermore, although not shown in FIG. 1, but disclosed in these other applications, the column level detectors 54/56 communicate with a computer for processing the data collected by these detectors.

Figure 2:
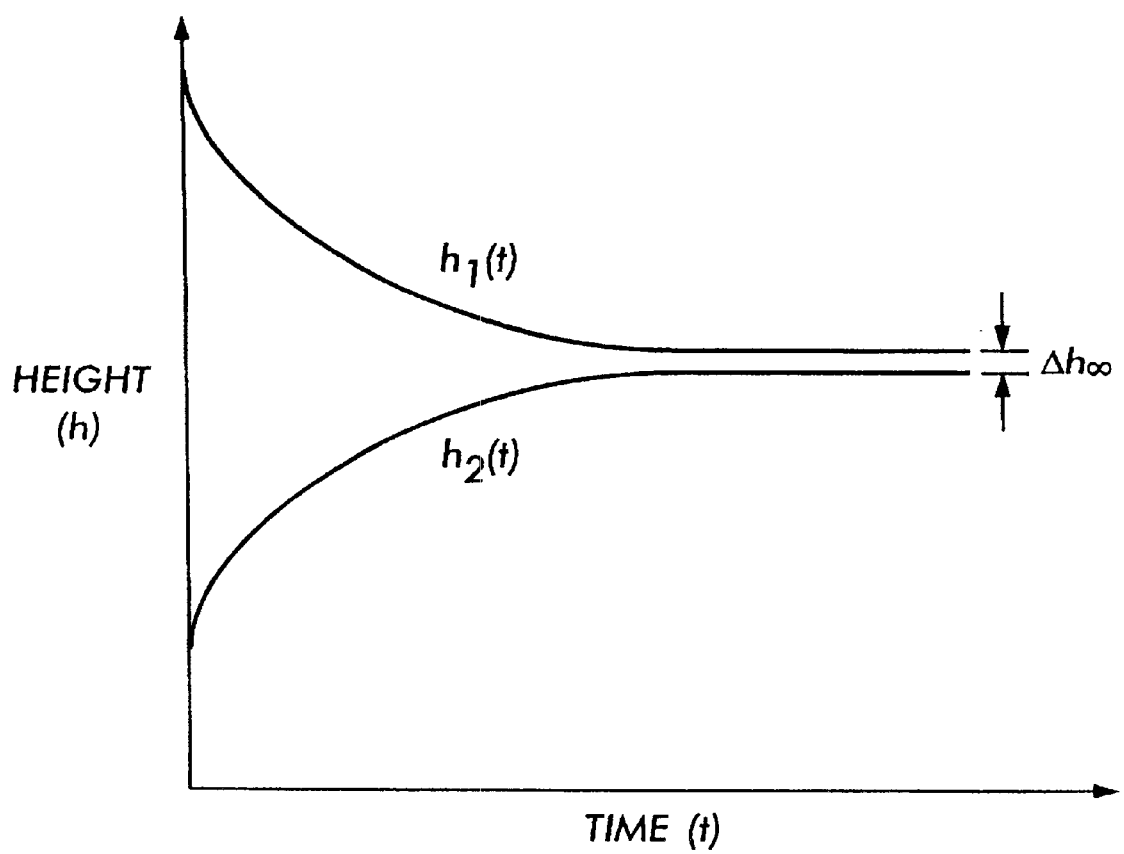
FIG. 2 is a graphical representation of the height of the respective columns of fluid over time in the two legs of the U-shaped tube.

It should be understood that it is within the broadest scope of this invention to include the monitoring of only one of the columns of fluid 82 or 84 while obtaining a single point from the other one of the columns of fluid 82 or 84 using a single point detector 954 (which also communicates with the computer mentioned previously). In particular, as shown in FIG. 2, since the rising and falling columns 82/84 exhibit a symmetry about a horizontal axis, it is possible to monitor only one of the columns of fluid while obtaining a single data point from the other column. For example, as shown in FIG. 1, the column level detector 56 can be used to monitor the rising column 84 while the single point detector 954 can be used to detect any one point of the falling column 82 in R1.

In the preferred embodiment, the U-tube structure 20 is in an upright position; the test fluid is entered into the top of one of the legs (e.g., R1) while the top of the other leg (e.g. R2) is exposed to atmospheric pressure. Using this configuration, the test fluid is subjected to a decreasing pressure differential that moves the test fluid through a plurality of shear rates (i.e., from a high shear rate at the beginning of the test run to a low shear rate at the end of the test run), which is especially important in determining the viscosity of non-Newtonian fluids, as set forth in application Ser. Nos. 09/439,795 and 09/573,267. However, it should be understood that it is within the broadest scope of this invention to include any other configurations where the test fluid can be subjected to a decreasing pressure differential in order to move the test fluid through a plurality of shear rates.

As disclosed in those patent applications, the height vs. time data that was generated is shown in FIG. 2, where as time goes to infinity a constant separation between the column heights, known as $\Delta h_\infty$ can be attributed to surface tension $\Delta h_{st}$ and/or yield stress $\tau_y$. The present application provides a method for determining the individual effects of these two parameters. In particular, the present application discloses a mathematical method to isolate both the effects of surface tension and yield stress of a test fluid from the pressure drop created by the height difference between the two columns of test fluid in respective legs of the U-shaped tube.

The method begins with the conservation of energy equation which can be written in terms of pressure as follows:

$$P_1 + \frac{1}{2}\rho V_1^2 + \rho g h_1(t) = P_2 + \frac{1}{2}\rho V_2^2 + \rho g h_2(t) + \Delta P_c + \rho g \Delta h_{st} \quad (1)$$

where $P_1$ and $P_2$: hydro-static pressures at fluid levels at the two columns 82/84 in the U-shaped tube;

$\rho$: density of fluid;

g: gravitational acceleration;

$V_1$ and $V_2$: flow velocities of the two columns of fluid 82/84 in the U-shaped tube; $h_1(t)$ and $h_2(t)$: heights of the two columns of fluid 82/84 in the U-shaped tube;

$\Delta P_c(t)$: pressure drop across the capillary tube 22;

$\Delta h_{st}$: additional height difference due to surface tension; Since $P_1$ and $P_2 = P_{atm}$ and $|V_1| = |V_2|$, equation (1) can be reduced to the following:

$$\Delta P_c(t) = \rho g [h_1(t) - h_2(t) - \Delta h_{st}] \quad (2)$$

This last equation demonstrates that the effect of the surface tension is isolated by subtracting $\Delta h_{st}$ from the height difference, $h_1(t) - h_2(t)$, between the two columns of fluid 82/84 in the U-shaped tube; the yield stress $\tau_y$ will be addressed later. Thus, the pressure drop across a capillary tube 22 can be determined as shown in Equation (2). Later, $\Delta h_{st}$ is determined through curve fitting of the experimental data of $h_1(t)$ and $h_2(t)$.

It should be understood that Equation 2 is valid regardless of the curve-fitting model selected, i.e., power-law, Casson, or Herschel-Bulkley model. Furthermore, as used throughout this Specification, the phrase "curve fitting" encompasses all manners of fitting the data to a curve and/or equation, including the use of "solvers", e.g., Microsoft's Excel Solver that can solve for a plurality of unknowns in a single equation from data that is provided.

When a fluid exhibits a yield stress ($\tau_y$), the height difference between the two fluid columns of the U-shaped tube is greatly affected by the yield stress particularly at low shear operation. Accordingly, the effect of the yield stress also must be taken into account (i.e., isolated) in order to accurately estimate the pressure drop across the capillary tube. In order to handle the yield stress term, one needs to start with a constitutive equation such as the Casson or Herschel-Bulkley model. These constitutive models have a term representing the yield stress as set forth below:

Casson model:

$$\sqrt{\tau} = \sqrt{\tau_y} + \sqrt{k}\dot{\gamma}, \text{ when } \tau > \tau_y$$

$$\dot{\gamma} = 0, \tau < \tau_y$$

where $\tau$ is shear stress, $\dot{\gamma}$ is shear rate, $\tau_y$ is the yield stress, and k is a constant.

Herschel-Bulkley model:

$$\tau = \tau_y + k\dot{\gamma}^n \text{ when } \tau \leq \tau_y$$

$$\dot{\gamma} = 0, \text{ when } \tau < \tau_y$$

where k and n are model constants.

It should be noted that the power-law model does not have the yield stress term. Thus, it does not have the capability of handling the effect of yield stress.

For both the Casson and Herschel-Bulkley models, the pressure drop across the capillary tube 22, $\Delta P_c(t)$, can be expressed as follows:

$$\Delta P_c(t) = \rho g [h_1(t) - h_2(t) - \Delta h_{st}] \quad (3)$$

As time goes to infinity, this equation can be written as $$\Delta P_c(\infty) = \rho g [h_1(\infty) - \Delta h_{st}] \quad (4)$$

where $\Delta P_c(\infty)$ represents the pressure drop across the capillary tube 22 as time goes to infinity, which can be attributed to the yield stress, $\tau_y$, of the test fluid. There is a relationship between the yield stress, $\tau_y$, and $\Delta P_c(\infty)$, which can be written as:

$$\tau_y = \frac{\Delta P_c(\infty) \cdot R}{2L} \quad (5)$$

where R and L are the radius and the length of the capillary tube 22, respectively.

To obtain the $\Delta h_{st}$ and $\tau_y$, two alternative approaches can be used. In the first approach, these two parameters are obtained sequentially, i.e., Equation 4 is curve-fitted using the experimental data of $h_1(t)$ and $h_2(t)$ data and solved for $\Delta h_{st}$; then the determined value for $\Delta h_{st}$ is plugged into Equation 5 and solved for $\tau_y$.

Alternatively, in the second approach, both $\Delta h_{st}$ and the yield stress can be determined directly from the curve fitting of the experimental data of $h_1(t)$ and $h_2(t)$, as set forth below. As mentioned previously, in order to handle the yield stress $\tau_y$, a constitutive equation is required, which has a term representing the yield stress. Examples of such a constitutive equation include Casson and Herschel-Bulkley models, although these are only by way of example and not limitation. In particular, the procedure for curve-fitting the column height data with either a Casson model or a Herschel-Bulkley model is as follows:

From the falling column of fluid 82, $h_1(t)$, and the rising column of fluid 84, $h_2(t)$, one can obtain the flow velocities of the two columns by taking the derivative of each height, i.e., $$V_1 = \frac{dh_1(t)}{dt} \quad \text{and} \quad (6)$$

$$V_2 = \frac{dh_2(t)}{dt} \quad (7)$$

Since the flows in the two columns of the U-shaped tube move in the opposite directions, one can determine the average flow velocity at the riser tube, $\overline{V}_r$, by the following equation:

$$V_r = \frac{1}{2}(V_1 - V_2) = \frac{1}{2}\left(\frac{dh_1(t)}{dt} - \frac{dh_2(t)}{dt}\right) \quad (8)$$

Since the scanning capillary tube viscometer collects $h_1(t)$ and $h_2(t)$ data over time, one can digitize the $h_1(t)$ and $h_2(t)$ data in the following manner to obtain the average flow velocity at the riser tube:

$$\frac{d(h_1(t) - h_2(t))}{dt} = \frac{(h_1(t+\Delta t) - h_2(t+\Delta t)) - (h_1(t-\Delta t) - h_2(t-\Delta t))}{2\Delta t} \quad (9)$$

In order to start a curve-fitting procedure, a mathematical description of $V_r$ is required for each model:

1. Casson model $$\sqrt{\tau} = \sqrt{\tau_y} + \sqrt{k\dot{\gamma}} \text{ when } \tau \geq \tau_y$$

$$\dot{\gamma} = 0, \text{ when } \tau < \tau_y$$

where $\tau$ is shear stress, $\dot{\gamma}$ is shear rate, $\tau_y$ is the yield stress, and k is a constant.

Wall shear stress ($\tau_w$) and yield stress ($\tau_y$) can be defined as follows:

$$\tau_w = \frac{\Delta P_c(t) \cdot R}{2L},$$

$$\tau_y = \frac{\Delta P_c(t) \cdot r_y(t)}{2L} \text{(evaluated as time goes to} \infty) = \frac{\Delta P_c(\infty) \cdot R}{2L},$$

where R and L are the radius and length of a capillary tube, respectively, and $r_y(t)$ is the radial distance, where shear stress ($\tau$) is bigger than yield stress ($\tau_y$).

Using the above equations, the velocity profile at the capillary tube 22 can be calculated as follows:

$$V(t, r) =$$

$$\frac{1}{4k} \cdot \frac{\Delta P_c(t)}{L}\left[R^2 - r^2 - \frac{8}{3}r_y^{\frac{1}{2}}(t)\left(R^{\frac{3}{2}} - r^{\frac{3}{2}}\right) + 2r_y(t)(R-r)\right] \text{ for } r_y(t) \leq r \leq$$

$$RV(t) = \frac{1}{4k} \cdot \frac{\Delta P_c(t)}{L}\left(\sqrt{R} - \sqrt{r_y(t)}\right)^3\left(\sqrt{R} + \frac{1}{3}\sqrt{r_y(t)}\right) \text{ for } r_y(t) \geq r$$

According to the definition of shear rate, $\dot{\gamma}$, the expression of the shear rate is defined as:

$$\dot{\gamma} = -\frac{dV}{dr} = \frac{1}{k}\left(\sqrt{\frac{\Delta P_c(t) \cdot r}{2L}} - \sqrt{\frac{\Delta P_c(t) \cdot r_y(t)}{2L}}\right).$$

In order to calculate the average flow velocity at either riser tube ($\overline{V}_r$), the flow rate at a capillary tube 22 needs to be determined first. The flow rate at the capillary tube 22 can be obtained by integrating the velocity profile over the cross-section of the capillary tube 22 as:

$$Q(t) = 2\pi \int_0^R Vr\,dr$$

$$= \frac{\pi R^4}{8k}\left[\frac{\Delta P_c(t)}{L} - \frac{16}{7} \cdot \left(\frac{2\tau_y}{R}\right)^{\frac{1}{2}}\left(\frac{\Delta P_c(t)}{L}\right)^{\frac{1}{2}} + \frac{4}{3}\left(\frac{2\tau_y}{R}\right) - \frac{1}{21} \cdot \left(\frac{2\tau_y}{R}\right)^4\left(\frac{\Delta P_c(t)}{L}\right)^{-3}\right].$$

Since $Q(t) = \pi R_r^2 \overline{V}_r$, the mean flow velocity at the riser tube can be calculated as follows:

$$\overline{V}_r = \frac{R^4}{8kR_r^2}\left[\frac{\Delta P_c(t)}{L} - \frac{16}{7} \cdot \left(\frac{2\tau_y}{R}\right)^{\frac{1}{2}}\left(\frac{\Delta P_c(t)}{L}\right)^{\frac{1}{2}} + \frac{4}{3} \cdot \left(\frac{2\tau_y}{R}\right) - \frac{1}{21} \cdot \left(\frac{2\tau_y}{R}\right)^4\left(\frac{\Delta P_c(t)}{L}\right)^{-3}\right]$$

where $R_r$ is the radius of either riser tube. Thus, a mathematical description for $\overline{V}_r$ for Casson model case is obtained.

Using a curve-fitting model (e.g., the Microsoft Excel Solver), the unknown variables can be determined. For the Casson model, there are three unknown variables, which are the model constant, k, the contribution of the surface tension $\Delta h_{st}$ and the yield stress $\tau_y$. It should be noted that the unknown variables are constants, which will be determined from the curve-fitting of experimental data of $\Delta P_c(t)$. It should also be noted that $\Delta P_c(t)$ essentially comes from $h_1(t)$ and $h_2(t)$ 2. Herschel-Bulkley model $$\tau = \tau_y + k\dot{\gamma}^n \text{ when } \tau \geq \tau_y$$

$$\dot{\gamma} = 0, \text{ when } \tau < \tau_y$$

where k and n are both model constants.

In a similar method as for the case of Casson model, the velocity profile at the capillary tube 22 can be derived for the Herschel-Bulkley model as follows:

$$V(t,r) = \left(\frac{\Delta P_c(t)}{2kL}\right)^{\frac{1}{n}} \left(\frac{n}{n+1}\right) \left[(R-r_y(t))^{\frac{n+1}{n}} - (r-r_y(t))^{\frac{n+1}{n}}\right] \text{ for } r_y(t) \leq r \leq R$$

$$V(t) = \left(\frac{\Delta P_c(t)}{2kL}\right)^{\frac{1}{n}} \left(\frac{n}{n+1}\right)(R-r_y(t))^{\frac{n+1}{n}} \text{ for } r_y(t) \geq r$$

The flow rate at capillary tube 22 can be obtained by integrating the velocity profile over the cross-section of the capillary tube 22 as:

$$Q(t) = 2\pi \int_0^R Vr\,dr$$

$$= \pi\left(\frac{\Delta P_c(t)}{2kL}\right)^{\frac{1}{n}}\left(\frac{n}{n+1}\right)R^{\frac{3n+1}{n}}\left(C_y^2(1-C_y)^{\frac{n+1}{n}} + \right.$$

$$(1+C_y)(1-C_y)^{\frac{2n+1}{n}} - \left(\frac{2n}{2n+1}\right)C_y(1-C_y)^{\frac{2n+1}{n}} -$$

$$\left.\left(\frac{2n}{3n+1}\right)(1-C_y)^{\frac{3n+1}{n}}\right)$$

where, $$C_y(t) = \frac{r_y(t)}{R},$$

which is used for convenience.
Since $Q(t) = \pi R_2^2 \overline{V}_r$, $$\overline{V}_r =$$

$$\left(\frac{1}{R_r^2}\right)\left(\frac{\Delta P_c(t)}{2kL}\right)^{\frac{1}{n}}\left(\frac{n}{n+1}\right)R^{\frac{3n+1}{n}}\left(C_y^2(1-C_y)^{\frac{n+1}{n}} + (1+C_y)(1-C_y)^{\frac{2n+1}{n}} - \right.$$

$$\left.\left(\frac{2n}{2n+1}\right)C_y(1-C_y)^{\frac{2n+1}{n}} - \left(\frac{2n}{3n+1}\right)(1-C_y)^{\frac{3n+1}{n}}\right)$$

where $R_r$ is the radius of either riser tube. Thus a mathematical description for $\overline{V}_r$ for the Herschel-Bulkley model case is obtained. Using a curve-fitting model (e.g., Microsoft Excel Solver), the unknown variables can be determined. For the Herschel-Bulkley model, there are four unknown variables, which are the two model constants, n and k, the contribution of the surface tension, $\Delta h_{st}$, and yield stress $\tau_y$. Again, it should be noted that the unknown variables are constants, which will be determined from the curve-fitting of experimental data of $\Delta P_c(t)$. It should also be noted that $\Delta P_c(t)$ essentially comes from $h_1(t)$ and $h_2(t)$.

It should be understood that the above disclosed methodology, including the equations, curve fitting, etc., can be implemented on the computer that communicates with the column level detectors 54/56 and/or the single point detector 954.

It should also be understood that the actual position of the flow restrictor 22 is not limited to the horizontal portion of the U-shaped tube; the flow restrictor 22 could form a portion of either leg of the U-shaped tube as shown in application Ser. Nos. 09/439,795 and 09/573,267.

Without further elaboration, the foregoing will so fully illustrate our invention that others may, by applying current or future knowledge, readily adopt the same for use under various conditions of service.

We claim:

1. A method for isolating the effect of surface tension on a fluid that is flowing in a U-shaped tube having a flow restrictor forming a portion of said U-shaped tube, said fluid forming a falling column of fluid, having a first height that changes with time, in a first leg of said U-shaped tube and a rising column of fluid, having a second height that changes with time, in a second leg of said U-shaped tube, said method comprising the steps of:

(a) detecting the difference between said first and second heights over time; and (b) subtracting a term representing surface tension from said difference.

2. The method of claim 1 wherein said step of detecting said difference between said first and second heights comprises monitoring the movement over time of at least one of said columns of fluid, while detecting a single data point of the other one of said columns of fluid for generating rising column data and falling column data.

3. The method of claim 2 wherein said at least one of said columns of fluid is said rising column of fluid and said other one of said columns of fluid is said falling column of fluid.

4. The method of claim 1 wherein said step of detecting the difference between said first and second heights comprises monitoring the movement of both of said columns of fluid over time for generating rising column data and falling column data.

5. The method of claim 4 wherein said step of subtracting a term representing surface tension comprises:

(a) selecting a first equation that represents a pressure drop across said flow restrictor in terms of said first and second heights; and (b) curve fitting said first equation using said rising column data and said falling column data to determine said term representing surface tension.

6. The method of claim 5 wherein said flow restrictor is a capillary tube of known dimensions and wherein said first equation comprises:

$$\Delta P_c(t) = \rho g\,[h_1(t) - h_2(t) - \Delta h_{st}],$$

where, $\Delta P_c(t)$ is said pressure drop across said capillary tube;

$\rho$ is the density of said fluid;

g is the gravitational acceleration;

$h_1(t)$ is said first height over time;

$h_2(t)$ is said second height over time; and $\Delta h_{st}$ is said term representing surface tension.

7. The method of claim 6 further comprising the step of determining the yield stress, $\tau_y$, of the fluid, said step of determining the yield stress comprises solving a second equation:

$$\tau_y = \frac{\Delta P_c(\infty) \cdot R}{2L},$$

where, $\Delta P_c(\infty)$ is given by: $\rho g[h_1(\infty) - h_2(\infty) - \Delta h_{st}]$;

$h_1(\infty)$ is said first height after a long period of time;

$h_2(\infty)$ is said second height after a long period of time;

R is the radius of said capillary tube; and

L is the length of said capillary tube.

8. The method of claim 2 wherein said step of subtracting a term representing surface tension comprises:

(a) selecting a first equation that represents a pressure drop across said flow restrictor in terms of said first and second heights; and (b) curve fitting said first equation using said rising column data and said falling column data to determine said term representing surface tension.

9. The method of claim 8 wherein said flow restrictor is a capillary tube of known dimensions and wherein said first equation comprises:

$$\Delta P_c(t) = \rho g[h_1(t) - h_2(t) - \Delta h_{st}],$$

where, $\Delta P_c(t)$ is said pressure drop across said capillary tube;

$\rho$ is the density of said fluid;

g is the gravitational acceleration;

$h_1(t)$ is said first height over time;

$h_2(t)$ is said second height over time; and $\Delta h_{st}$ is said term representing surface tension.

10. The method of claim 9 further comprising the step of determining the yield stress, $\tau_y$, of the fluid, said step of determining the yield stress comprises solving a second equation:

$$\tau_y = \frac{\Delta P_c(\infty) \cdot R}{2L},$$

where, $\Delta P_c(\infty)$ is given by: $\rho g[h_1(\infty) - h_2(\infty) - \Delta h_{st}]$;

$h_1(\infty)$ is said first height after a long period of time;

$h_2(\infty)$ is said second height after a long period of time;

R is the radius of said capillary tube; and

L is the length of said capillary tube.

11. A method of isolating the effect of surface tension on a fluid and the effect of yield stress of a fluid that is flowing in a U-shaped tube having a flow restrictor forming a portion of said U-shaped tube, said fluid forming a falling column of fluid, having a first height that changes with time, in a first leg of said U-shaped tube and a rising column of fluid, having a second height that changes with time, in a second leg of said U-shaped tube, said method comprising the steps of:

(a) detecting the difference between said first and second heights over time for generating falling column data and rising column data;

(b) curve fitting an equation using said falling column data and said rising column data to determine:
  (1) a term representing surface tension; and
  (2) a term representing said yield stress.

12. The method of claim 11 wherein said equation comprises a representation of the average velocity of either said falling column or said rising column of fluid.

13. The method of claim 12 wherein said equation utilizes a Casson model that defines fluid shear stress, $\tau$, in terms of yield stress, $\tau_y$, and shear rate $\dot{\gamma}$, as follows:

$$\sqrt{\tau} = \sqrt{\tau_y} + \sqrt{k}\dot{\gamma} \text{ when } \tau \geq \tau_y \text{ and}$$

$$\dot{\gamma} = 0 \text{ when } \tau < \tau_y; \text{ and}$$

where k is a model constant.

14. The method of claim 13 wherein said flow restrictor is a capillary tube of known dimensions and wherein said equation representing said velocity of either said falling column or said rising column is defined as:

$$V = \frac{R^4}{8kR_r^2} \left[ \frac{\Delta P_{c(t)}}{L} - \frac{16}{7} \cdot \left(\frac{2\tau_y}{R}\right)^{\frac{1}{2}} \left(\frac{\Delta P_c(t)}{L}\right)^{\frac{1}{2}} + \frac{4}{3} \cdot \left(\frac{2\tau_y}{R}\right) - \frac{1}{21} \cdot \left(\frac{2\tau_y}{R}\right)^4 \left(\frac{\Delta P_c(t)}{L}\right)^{-3} \right],$$

where:

R is the radius of said capillary tube;

L is the length of said capillary tube;

$R_r$ is the radius of said falling column of fluid or said rising column of fluid; and $\Delta P_c(t) = \rho g[h_1(t) - h_2(t) - \Delta h_{st}]$;

where:

$\Delta P_c(t)$ is a pressure drop across said capillary tube;

$\rho$ is the density of said fluid;

g is the gravitational acceleration;

$h_1(t)$ is said first height over time;

$h_2(t)$ is said second height over time; and $\Delta h_{st}$ is said term representing surface tension.

15. The method of claim 12 wherein said equation utilizes a Herschel-Bulkley model that defines fluid shear stress, $\tau$, in terms of yield stress, $\tau_y$, and shear rate $\dot{\gamma}$, as follows:

$$\tau = \tau_y + k\dot{\gamma}^n \text{ when } \tau \geq \tau_y \text{ and}$$

$$\dot{\gamma} = 0 \text{ when } \tau < \tau_y; \text{ and}$$

where k and n are model constants.

16. The method of claim 15 wherein said flow restrictor is a capillary tube of known dimensions and wherein said equation representing said velocity (V) of either said falling column or said rising column is defined as:

$$V = \left(\frac{1}{R_r^2}\right)\left(\frac{\Delta P_c(t)}{2kL}\right)^{\frac{1}{n}}\left(\frac{n}{n+1}\right)R^{\frac{3n+1}{n}}\left(C_y^2(1-C_y)^{\frac{n+1}{n}} + (1+C_y)(1-C_y)^{\frac{2n+1}{n}} - \left(\frac{2n}{2n+1}\right)C_y(1-C_y)^{\frac{2n+1}{n}} - \left(\frac{2n}{3n+1}\right)(1-C_y)^{\frac{3n+1}{n}}\right),$$

where:

$$C_y(t) = \frac{r_y(t)}{R};$$

R is the radius of said capillary tube;

$r_y(t)$ is the radial distance and where $\tau > \tau_y$;

L is the length of said capillary tube;

$R_r$ is the radius of said falling column of fluid or said rising column of fluid; and $\Delta P_c(t) = \rho g[h_1(t) - h_2(t) - \Delta h_{st}]$;

where:

$\Delta P_c(t)$ is a pressure drop across said capillary tube;

$\rho$ is the density of said fluid;

g is the gravitational acceleration;

$h_1(t)$ is said first height over time;

$h_2(t)$ is said second height over time; and $\Delta h_{st}$ is said term representing surface tension.

* * * * *